US005538845A

United States Patent [19]

Knops et al.

[11] Patent Number: 5,538,845
[45] Date of Patent: Jul. 23, 1996

[54] BETA-AMYLOID PEPTIDE PRODUCTION INHIBITORS AND METHODS FOR THEIR IDENTIFICATION

[75] Inventors: Jeroen Knops; Sukanto Sinha, both of San Francisco, Calif.

[73] Assignees: Athena Neurosciences, Inc., So. San Francisco, Calif.; Eli Lilly and Company, Indianapolis, Ind.

[21] Appl. No.: 831,722

[22] Filed: Feb. 5, 1992

[51] Int. Cl.[6] .................. G01N 33/567; G01N 33/544; G01N 33/545; C12Q 1/68
[52] U.S. Cl. ................ 435/6; 435/7.21; 435/69.2; 435/183; 436/530; 436/531; 530/387.1
[58] Field of Search .............. 435/29, 4, 3, 69.1, 435/70.3, 7.21, 6, 7.92, 69.2, 183, 184; 530/350, 361, 83.9; 436/518, 528, 529, 530, 531

[56] References Cited

U.S. PATENT DOCUMENTS 5,221,607  6/1993  Cordell et al. ............................ 435/6

OTHER PUBLICATIONS

Kang et al. (1987) Nature 325:773–776.
Ponte et al. (1988) Nature 331:525–527.
Kitaguchi et al. (1988) Nature 331:530–532.
Weidemann et al. (1989) Cell 57:115–126.
Oltersdorf et al. (1990) J. Biol. Chem. 265:4492–4497.
Esch et al. (1990) Science 248:1122–1124.
Tamoake et al. (1991) Am. Assoc. Neuropathol. Abstr. 149
Golde et al. (1991) Soc. Neuroscience Abstr. 17:1293.
Tamaoka et al. (1992) Proc. Natl. Acad. Sci. USA 89:1345–1349.
Knops et al. "Evidence for a Nonsecretory Acidic Degradation Pathway for Amyloid Precursor Protein in 293 cells", J. Biol. Chem., 267(23):16022–16024 (Aug. 15, 1992).
Ezzell, "Alzheimer's Alchemy", Science News, 141: 152–153 (Mar. 7, 1992).
Morris et al. "The Consortium to Establish a Registry for Alzheimer's Disease (CERAD)", Neurobiology, 39:1159–1165 (Sep. 1989).
Yankner et al, "Neurotoxicity of a Fragment of the Amyloid Precursor Associated with Alzheimer's Disease", Science 245:417–420 (28 Jul. 1989).
M. A. Winkler, "Tacrine for Alzheimer's Disease", JAMA, 271(13): 1023–1024 Apr. 6, 1994.

*Primary Examiner*—Toni R. Scheiner
*Assistant Examiner*—Patricia A. Duffy
*Attorney, Agent, or Firm*—Townsend and Towsend and Crew

[57] ABSTRACT

A method for identifying compounds capable of inhibiting the production of β-amyloid peptide in cells comprises exposing cultured cells in one or more test compounds. The cells are cultured under conditions which produce amyloid precursor protein and which result in intracellular accumulation of an approximately 22 kD polypeptide which includes the entire sequence of the β-amyloid peptide. Test compounds which cause a change in the accumulation of the 22 kD polypeptide are considered likely candidates for use as drugs for treating β-amyloid diseases, such as Alzheimer's disease.

38 Claims, 3 Drawing Sheets

BETA-AMYLOID PEPTIDE PRODUCTION INHIBITORS AND METHODS FOR THEIR IDENTIFICATION

BACKGROUND OF THE INVENTION

1. Field of the invention

The present invention relates generally to compounds and methods for identifying compounds which have a biological activity. More particularly, the present invention relates to methods for identifying compounds capable of inhibiting the production of β-amyloid peptide in cells.

Alzheimer's disease is a neurodegenerative brain disorder which typically leads to progressive memory loss, dementia, and finally death. It is the fourth leading cause of death in the United States, responsible for approximately 100,000 deaths annually. Alzheimer's disease primarily afflicts the elderly and is expected to be an increasing health care concern in the future with the aging of the United States population. At present, there are no proven means for diagnosis, prevention, treatment, or cure of Alzheimer's disease.

Alzheimer's disease is characterized by the presence of numerous amyloid plaques and neurofibrillary tangles (highly insoluble protein aggregates) present in the brains of Alzheimer's disease patients, particularly in those regions involved with memory and cognition. While in the past there was significant scientific debate over whether the plaques and tangles are a cause or are merely the result of Alzheimer's disease, recent discoveries indicate that amyloid plaque is a causative precursor or factor. In particular, it has been discovered that the production of β-amyloid peptides, a major constituent of the amyloid plaque, can result from mutation in the gene encoding amyloid precursor protein, a protein which when normally processed will not produce the β-amyloid peptide. Moreover, β-amyloid peptide is toxic to brain neurons, and neuronal cell death is associated with the disease.

Thus, it is believed that a drug that could interfere with β-amyloid plaque formation or toxicity may delay or halt the progression of Alzheimer's disease. At present, no suitable in vitro systems or methods exist for screening candidate drugs for the ability to inhibit or prevent the production of β-amyloid plaque. The scarcity of such screening methods may, at least in part, result from insufficient understanding of the pathogenic mechanism(s) which cause the conversion of amyloid precursor protein to the β-amyloid peptide, and ultimately to the amyloid plaque.

For these reasons, it would be desirable to provide methods and systems for screening test compounds for the ability to inhibit or prevent the conversion of amyloid precursor protein to β-amyloid peptide. In particular, it would be desirable to base such methods and systems on a metabolic pathway which is involved in such conversion, where the test compound would be able to interrupt or interfere with the metabolic pathway which leads to conversion. Such methods and systems should be rapid, economical, and suitable for screening large numbers of test compounds. In particular, initial methods should utilize in vitro systems rather than animal models, so that the methods are particularly suitable for initial screening of test compounds to identify suitable candidate drugs.

2. Description of the Background Art

β-amyloid peptide (also referred to as A4 or AβP) is derived from amyloid precursor protein, which is expressed in differently spliced forms of 695, 751, and 770 amino acids. See, Kang et al. (1987) Nature 325:773–776; Ponte et al. (1988) Nature 331:525–527; and Kitaguchi et al. (1988) Nature 331:530–532. Normal processing of amyloid precursor protein involves proteolytic cleavage at a site between residues 16 and 17 (as numbered starting with $Asp_{597}$ as residue 1) near the transmembrane domain, resulting in the constitutive secretion of an extracellular domain and the appearance of an intracellular fragment (approximately 9 kilodalton (kD)), referred to as the constitutive carboxy-terminal fragment (cCTF). This pathway appears to be widely conserved among species and present in many cell types. See, Weidemann et al. (1989) Cell 57:115–126; Oltersdorf et al. (1990) J. Biol. Chem. 265:4492–4497; and Esch et al. (1990) Science 248:1122–1124. This normal pathway cleaves within the region of the precursor protein which corresponds to the β-amyloid peptide, thus apparently precluding its formation.

Tamaoka et al. (1991) Am. Assoc. Neuropathol. Abstr. 149, report the identification of an approximately 22 kD fragment of amyloid precursor protein microvessel fractions from human cerebral cortex labelled by four distinct antisera to amyloid precursor protein C-terminal peptides as well as by antibodies raised to fusion proteins containing residues 444–592 (αBX5) and residues 595–695 (αBX6) of amyloid precursor protein.

Golde et al. (1991) Soc. Neuroscience Abstr. 17:1293, identify a set of carboxy-terminal fragments of amyloid precursor protein ranging in molecular weights from 8 to 12 kD, the largest of which the authors believe may contain the entire β-amyloid peptide sequence and which is produced in the normal processing of amyloid precursor protein in 293 cells (a human kidney cell line) overexpressing amyloid precursor protein.

SUMMARY OF THE INVENTION

The present invention provides methods for identifying compounds which inhibit the production of β-amyloid peptide in animal cells. In particular, the methods rely on exposing cultured cells capable of producing amyloid precursor protein to test compounds, where the cell culture conditions are selected to cause intracellular accumulation of an approximately 22 kD polypeptide which includes a sequence corresponding to the entire β-amyloid peptide. Typically, the culture conditions comprise exposing the cultured cells to a substance which enhances the intracellular accumulation of the 22 kD polypeptide, usually a protease inhibitor. The 22 kD polypeptide is a processing intermediate of the β-amyloid peptide, and compounds which are able to inhibit or interfere with its further processing to the β-amyloid peptide are candidates for treating Alzheimer's disease and other conditions which may result from amyloid plaque deposition. This polypeptide is referred to hereinafter and in the claims as the "22 kD preamyloid intermediate" polypeptide.

In addition to the identification and screening aspects discussed above, the present invention comprises pharmaceutical compositions comprising compounds selected by these methods, as well as methods for inhibiting β-amyloid peptide production by administration of these compounds to cells and patients. The present invention further comprises purified and isolated forms of the 22 kD preamyloid intermediate polypeptide.

DESCRIPTION OF THE SPECIFIC EMBODIMENTS

The present invention results from the discovery of a novel approximately 22 kilodalton (kD) polypeptide which appears to be a processing intermediate in the production of β-amyloid peptide which is a causative factor of Alzheimer's disease. The precise molecular weight of the peptide is not known, but is believed to be within the range from 21 kD to 25 kD and is probably within the range from 21.5 kD to 23 kD. For convenience, the peptide will be referred to hereinafter as the approximately 22 kD preamyloid intermediate polypeptide, but it will be appreciated that the actual molecular weight may be different. The approximately 22 kD peptide is further characterized by the electrophoretic mobility patterns set forth in FIGS. 2–4, which are described in detail in the Experimental section hereinafter.

Figure 1:
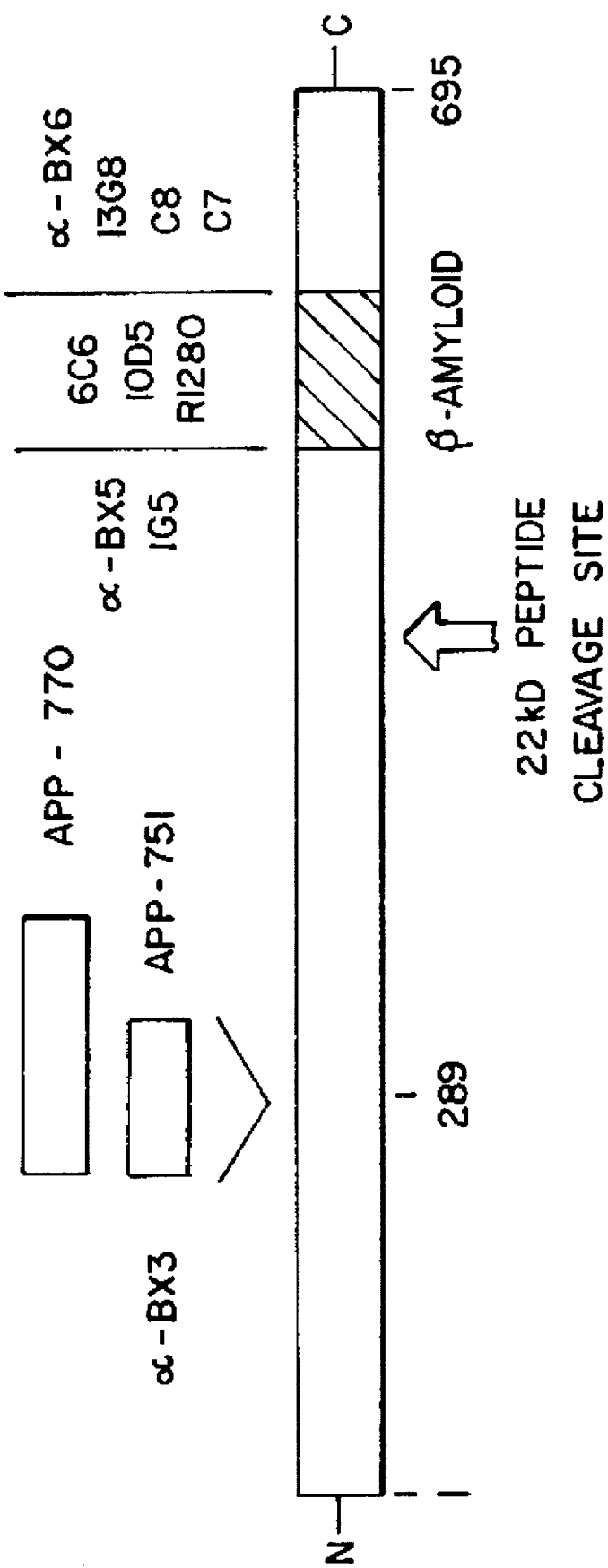
FIG. 1 is a map of the 695 amino acid isoform of the amyloid precursor protein showing (1) the insertion site for the 751 and 771 isoforms, (2) the approximate location of the 22 kD peptide cleavage site, (3) the β-amyloid region, and (4) the relative positions of the binding sites for the following antibodies: α-BX3; α-BX5; α-BX6; 6C6; 1G5; 10D5; R1280; 13G8; C8; and C7.

The approximately 22 kD preamyloid intermediate polypeptide contains the entire β-amyloid peptide sequence and results from cleavage of the various isoforms of amyloid precursor protein at a site believed to be located from about 85 to 65 residues on the N-terminal side of the β-amyloid sequence. With reference to FIG. 1, it can be seen that the β-amyloid sequence is approximately 42 amino acids in length and located near the C-terminus of each of the isoforms (695, 751, and 770). Cleavage occurs approximately where indicated by the arrow (↑), and it is believed that the cleavage occurs as the result of enzymatic processing which is part of an alternative degradative pathway of amyloid precursor protein. The alternative pathway appears to occur in an acid compartment, probably an endosomal/lysosomal compartment, and is part of normal (non-pathogenic) cellular processes. It is believed that the existence of the approximately 22 kD preamyloid intermediate polypeptide has not previously been observed because of rapid degradation which occurs in the absence of steps taken to cause its accumulation, as will be described hereinafter. While the 22 kD preamyloid intermediate polypeptide is believed to be a normal cellular processing intermediate, it is further believed that the polypeptide is involved in the pathogenic production of β-amyloid peptide in diseased cells of Alzheimer's patients.

The present invention comprises the isolated and purified 22 kD preamyloid intermediate polypeptide itself as well as methods for identifying drugs and compounds capable of inhibiting its production or its conversion to β-amyloid peptide. The polypeptide compositions are obtained in substantially pure form, that is, typically from about 50% w/w (weight/weight) or more purity, and are substantially free from interfering proteins and contaminants. Preferably, the 22 kD preamyloid intermediate polypeptides are isolated or synthesized in a purity as high as about 80% w/w or higher. Using conventional protein purification techniques, homogeneous polypeptide compositions of at least about 50% w/w purity can be obtained from cellular sources which are treated to enhance production of the 22 kD polypeptide, as described hereinafter. For example, the 22 kD polypeptides may be purified by use of the antibodies subscribed hereinafter using the immunoadsorbent affinity columns prepared by conventional techniques.

The identification of compounds and drugs capable of inhibiting either the formation of the 22 kD polypeptide, or its conversion to β-amyloid peptide, would thus be valuable in the search for drugs suitable for treating Alzheimer's disease and related conditions. According to the present invention, such screening and identification tests comprise exposing cultured cells to test compounds and observing whether production of the novel approximately 22 kD preamyloid intermediate polypeptide is affected. The cells are cultured under conditions which (in the absence of effective test compounds) result in the intracellular accumulation of the 22 kD polypeptide, typically relying on the addition of one or more protease inhibitor(s) to slow the intracellular degradation of the polypeptide. The test compounds are exposed to the test cells under such conditions and are evaluated for the ability either to inhibit formation of the 22 kD preamyloid intermediate polypeptide or to prevent its degradation (i.e. enhance its intracellular accumulation). Compounds with either ability are candidates for further screening in animal models, or otherwise, for the ability to inhibit β-amyloid peptide production and deposition.

Cells suitable for culturing in the methods of the present invention will usually be mammalian cell lines, more usually being human cell lines, available from many sources, such as the American Type Culture Collection, Rockville, Md. 20852. Suitable cell types for transformation as well as for use as primary cultures include kidney cells, neuronal cells, adrenal cells, Chinese hamster ovary cells, and the like. An exemplary transformed human embryonic kidney cell line is the human 293 cell line, ATCC accession number CRL-1573.

The cell lines may be modified to overexpress at least one isoform of amyloid precursor protein. The amyloid precursor protein gene is located on chromosome 21, and cloning of the 695 isoform (cDNA) is reported in Kang et al. (1987) Nature 325:733–738, the disclosure of which is incorporated herein by reference. cDNA clones of the 751 amino acid and 770 amino acid isoforms of amyloid precursor protein are also reported in Tanzi et al. (1988) Nature 331:528–530 and Kitaguchi et al. (1988) Nature 331:530–532, respectively. The disclosures of both of these references are incorporated herein by reference. The transfection of human 293 cells with the 751 amino acid isoform is reported in Oltersdorf et al. (1990) J. Biol. Chem. 265:4492–4497, the disclosure of which is further incorporated herein by reference. Use of the transfected human 293 cells in the methods of the present invention is described in detail in the Experimental Section hereinafter.

Cells from the chosen cell line will be cultured under conditions suitable for the cell line. Generally, a basal medium such as Dulbecco's Modified Eagle Medium, supplemented with serum such as fetal bovine serum, antibiotics, and the like, will be used. After cell growth has been established, the cells will be exposed to conditions which cause or permit the accumulation of the approximately 22 kD preamyloid intermediate polypeptide of the present invention. Typically, the conditions comprise the addition of protease inhibitor(s) capable of inhibiting degradation of the approximately 22 kD preamyloid intermediate polypeptide to permit the desired intracellular accumulation.

Suitable protease inhibitors include lysosomal cysteine protease inhibits, such as leupeptin (Ac-Leu-Leu-Arg-CHO); E-64 (L-trans-3-carboxyoxiran-2-carbonyl-L-leucylagmatin); and L-trans epoxysuccinyl-L-leucylamido-3-methyl-butaine, all of which are available from Sigma Chemical Co., St. Louis, Mo. For many cell lines, it may be desirable or necessary to combine effective or potentiating amounts of two or more other protease inhibitors, such as aspartic protease inhibitors, e.g., pepstatin, and the like. These and other suitable protease inhibitors are described in Rich, "Inhibitors of Aspartic Acid Proteases" in: Proteinase Inhibitors, Barrett and Salveson, Eds., Elsvier Press (1985), pp. 153–178, the disclosure of which is incorporated herein by reference.

Such protease inhibitors will typically be present in the culture medium at a concentration from about 0.1 µM to 1 mM, usually from about 1 µM to 0.1 mM.

While the culture continues under the conditions which cause the accumulation of the approximately 22 kD preamyloid intermediate polypeptide, the cells are exposed to test compounds and the effect, if any, on such intracellular accumulation is determined after a preselected time period, usually from about 0.5 to 10 hours. The test compounds can be any molecule, compound, or other substance which can be added to the cell culture without substantially interfering with cell viability. Suitable tests compounds may be small molecules, biological polymers, such as polypeptides, polysaccharides, polynucleotides, and the like. Of particular interest will be protease inhibitors, lysosomotropic bases, proton adenosine triphosphatase inhibitors, and other candidate drugs which do not affect secretion of the amyloid precursor protein, which are not toxic to the cells or when administered to the host, and the like.

The test compounds will typically be administered to a concentration in the range from about 1 µM to 1 mM, usually from about 10 µM to 1 mM.

In order to determine the effect of the test compound on the accumulation of the approximately 22 kD preamyloid intermediate polypeptide, the test cells will be subjected to conventional protein analysis techniques for semi-quantitatively or quantitatively determining the amount of the polypeptide in the cultured cells. Conveniently, the polypeptide content will be analyzed by conventional pulse-chase analysis where test and control cells are cultured in the presence of radio-labelled amino acids (e.g. $^{35}$S-methionine) for a preselected period of time, typically about one hour, under the conditions necessary for causing the accumulation of the 22 kD preamyloid intermediate polypeptide. After such a "pulse" of radio-label, the cells are cultured in fresh medium while the conditions necessary for polypeptide accumulation are maintained. After a period of time sufficient for expression of the amyloid precursor protein and degradation of protein to the 22 kD polypeptide, typically from about 2 to 10 hours but which may be from 0.5 to 24 hours depending on the cell type, the cells are harvested and protein determinations performed.

Protein determinations will typically be performed by lysing harvested cells to release and solubilize their cellular contents, immunoprecipitation using antibodies capable of binding to the 22 kD preamyloid intermediate polypeptide, and gel electrophoresis to separate the different polypeptides. Suitable antibodies include 13G8, C8, C7, 10D5, R1280, α-BX 6, and 1G5, as described in more detail in the Experimental section hereinafter.

The amount of 22 kD preamyloid intermediate protein can be estimated by the band intensity on an autoradiograph taken from the separation gel. Specific methods for performing such an immunoprecipitation and electrophoresis analysis are described in detail in the Experimental section hereinafter. Other methods for determining the presence and quantity of the 22 kD preamyloid intermediate polypeptide in the cellular samples will be readily apparent to those skilled in the art.

Usually, the tests will be run by comparing the accumulation of the approximately 22 kD peptide in test cells exposed to the test compound(s) with such accumulation in control cells which are cultured for the same time and under identical conditions (except for the absence of the test compound). It will thus be possible to directly determine whether the test compound has had an effect on accumulation.

As discussed above, test compounds which are able to either inhibit accumulation or enhance accumulation will be considered as candidates for further determinations of the ability to block β-amyloid production in pathogenic cells. Inhibition of accumulation indicates that production of the 22 kD polypeptide has been at least partly blocked, reducing the amount of processing intermediate available for conversion to β-amyloid peptide. Enhanced accumulation indicates that conversion of the 22 kD polypeptide to β-amyloid peptide (or other products) is being at least partly blocked. In either case, the test compound has displayed an activity which is potentially beneficial in blocking the production and deposition of β-amyloid peptide.

The present invention further comprises methods for inhibiting β-amyloid production in cells, where the method include administering to the cells compounds selected by the method described above. The compounds may be added to cell culture in order to inhibit β-amyloid production by the cultured cells. The compounds may also be administered to a patient in order to inhibit the deposition of amyloid plaque associated with Alzheimer's disease.

The present invention further comprises pharmaceutical compositions incorporating a compound selected by the above-described method and including in a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference.

The pharmaceutical compositions just described are suitable for systemic administration to the host, including both parenteral and oral administration. The pharmaceutical compositions may be administered parenterally, i.e. subcutaneously, intramuscularly, or intravenously. Thus, the present invention provides compositions for administration to a host, where the compositions comprise a pharmaceutically acceptable solution of the identified compound in an acceptable carrier, as described above.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The concentration of the compound in the pharmaceutical carrier may vary widely, i.e. from less than about 0.1% by weight of the pharmaceutical composition to about 20% by weight, or greater. Typical pharmaceutical composition for intramuscular injection would be made up to contain, for example, one to four ml of sterile buffered water and one µg to one mg of the compound identified by the method of the present invention. The typical composition for intravenous infusion could be made up to contain 100 to 500 ml of sterile Ringer's solution and about 1 to 100 mg of the compound.

The pharmaceutical compositions of the present invention can be administered for prophylactic and/or therapeutic treatment of diseases related to the deposition of β-amyloid peptide, such as Alzheimer's disease. In therapeutic applications, the pharmaceutical compositions are administered to a host already suffering from the disease. The pharmaceutical compositions will be administered in an amount sufficient to inhibit further deposition of β-amyloid plaque. An amount adequate to accomplish this is defined as a "therapeutically effective dose." Such effective dose will depend on the extent of the disease, the size of the host, and the like, but will generally range from about 0.01 µg to 10 mg of the compound per kilogram of body weight of the host, with dosages of 0.1 µg to 1 mg/kg being more commonly employed.

For prophylactic applications, the pharmaceutical compositions of the present invention are administered to a host susceptible to the β-amyloid disease, but not already suffering from such disease. Such hosts may be identified by genetic screening and clinical analysis, as described in the medical literature. The pharmaceutical compositions will be able to inhibit or prevent deposition of the β-amyloid plaque at a very early stage, preferably preventing even the initial stages of the β-amyloid disease. The amount of the compound required for such prophylactic treatment, referred to as a prophylactically-effective dosage, are generally the same as described above for therapeutic treatment.

The following examples are offered by way of illustration, not by way of limitation.

EXPERIMENTAL

Example 1

Detection of the 22 kD fragment of amyloid precursor protein.

Cells from the 293 cell line (a transformed human embryonic kidney cell line; ATCC accession no. CRL-1573) which had been stably transfected with cDNA encoding the 751 amino acid form of amyloid precursor protein (according to the method of Oltersdorf et al. (1990) J. Biol. Chem. 265:4492–4497) were grown in Dulbecco's Modified Eagle medium (DMEM) containing 4.5 g/L D-glucose, supplemented with 10% heat-inactivated fetal bovine serum (FBS) and 400 µg/ml geneticin sulfate. The cells were split, and then plated in 6 well culture dishes at approximately $5 \times 10^5$ cells/ml and 3 ml/well. Conditioned medium from subconfluent cells was removed from each well after 16 hours, then replaced with fresh medium supplemented with either 0.1 mM leupeptin (Ac-Leu-Leu-Arg-CHO; Sigma Chemical Co., St. Louis, Mo.) or 0.1 mM E-64 (epoxysuccinyl-leucylagmatine; Sigma). After an additional 16 hours, the medium was removed, and the cells methionine starved for 30 minutes in methionine-free DMEM. The medium was again replaced, supplemented with 100 µCi/mL $^{35}$S-methionine (Amersham Corp., Arlington Heights, Ill.) and either 0.1 mM leupeptin or 0.1 mM E-64, and the cells metabolically labelled for 1 hour at 37° C. The labelling medium was then removed, the cells washed twice with fresh medium, then chased for 2, 4, 8 or 24 hours in DMEM-F12 (1:1) medium supplemented with 50 µM ethanolamine and 10 nM sodium selenite, in the presence of the appropriate inhibitor. Control cells were treated exactly as described, except no inhibitor was added at any time. Some wells were harvested immediately after the end of the labelling period ("0" chase).

For immunoprecipitation analyses, approximately $2 \times 10^6$ cells were lysed in 1 mL of ice-cold lysis buffer (50 mM Tris, pH 8, 0.15N NaCl, 20 mM Na-EDTA, 1% sodium deoxycholate, 1% Triton® X-100, and 0.1% SDS). The lysates were cleared of non-lysed cells, nuclei, and cell debris by centrifugation at 100,000×g and 4° C. for 5 minutes. The resulting supernatants are referred to as "extracts." Aliquots of the various extracts containing 40 µg total protein (measured by the BCA protein assay described in Smith et al. (1985) Anal. Biochem. 150: 76–85) were then incubated with 5 µg of purified anti-BX6 (Oltersdorf et al. (1990) supra.; see FIG. 1 for approximate binding location), and immunoprecipitated with 20 µL of 50% (v/v) protein A-Sepharose (Pharmacia, Piscatacay, N.J.), pre-swollen in PBS, with end-over-end agitation for 2 hours at 4° C. The cleared extracts were removed from the immunoprecipitates by centrifugation at 15,000 =g for 10 minutes at 4° C. The immunoprecipitates were washed three times with ice-cold TBS containing 5 mM sodium-EDTA and 0.5% NP-40. The immunoprecipitated proteins were solubilized by boiling each sample with two volumes of 2×Laemmli reducing sample buffer, and separated by electrophoresis on 10–20% Tris-Tricine gradient gels (Novex, Encitas, Calif.). Following electrophoresis, the gels were fixed in 25% 2-propanol, 10% acetic acid, soaked in Amplify (Amersham), dried and exposed to Kodak X-AR autoradiography film (Rochester, N.Y.).

In order to visualize secreted amyloid precursor protein, the conditioned medium obtained at each chase time was further immunoprecipitated with anti-BX5 (Oltersdorf et al. (1990), supra.). In each case, a volume of medium corresponding to the total protein used in the cells was directly treated with 5 µg anti-BX5, then the protocol described above for cell extract immunoprecipitations was followed exactly.

Figure 2A:
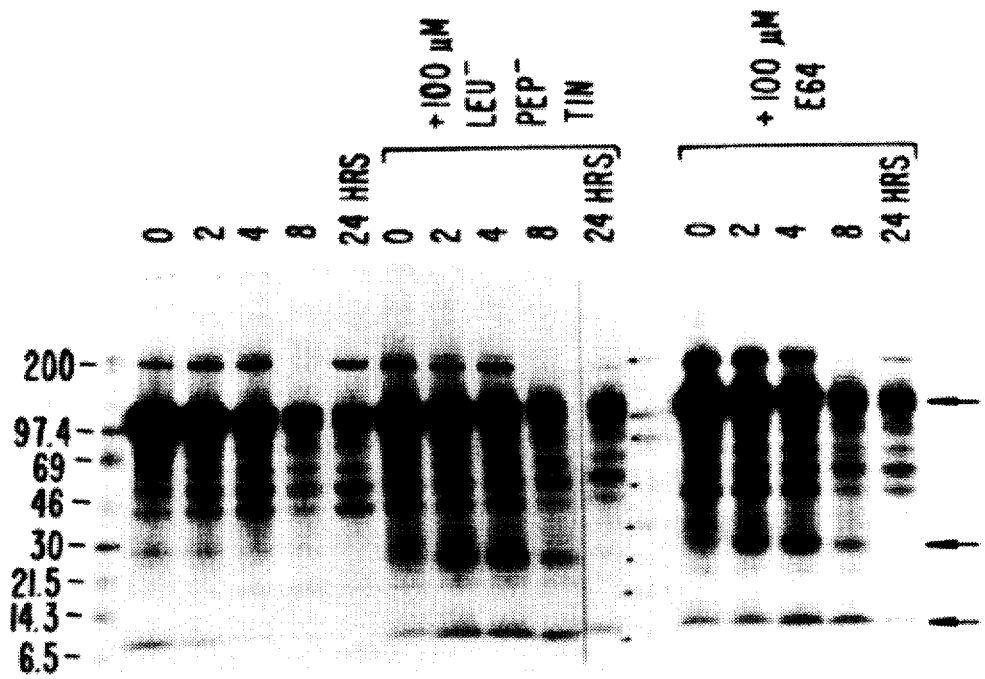
FIGS. 2A and 2B are electrophoretic gel autoradiographs which illustrate a band at approximately 22 kD, which represents the 22 kD preamyloid intermediate polypeptide of the present invention, as described in detail in the Experimental section hereinafter. The molecular weight standards used were obtained from Amersham catalogue no. CFA 626 ($^{14}$C methylated protein, MW 14,300–200,000) and CFA 645 ($^{14}$C methylated protein, MW 2550–30,000).
Figure 2B:
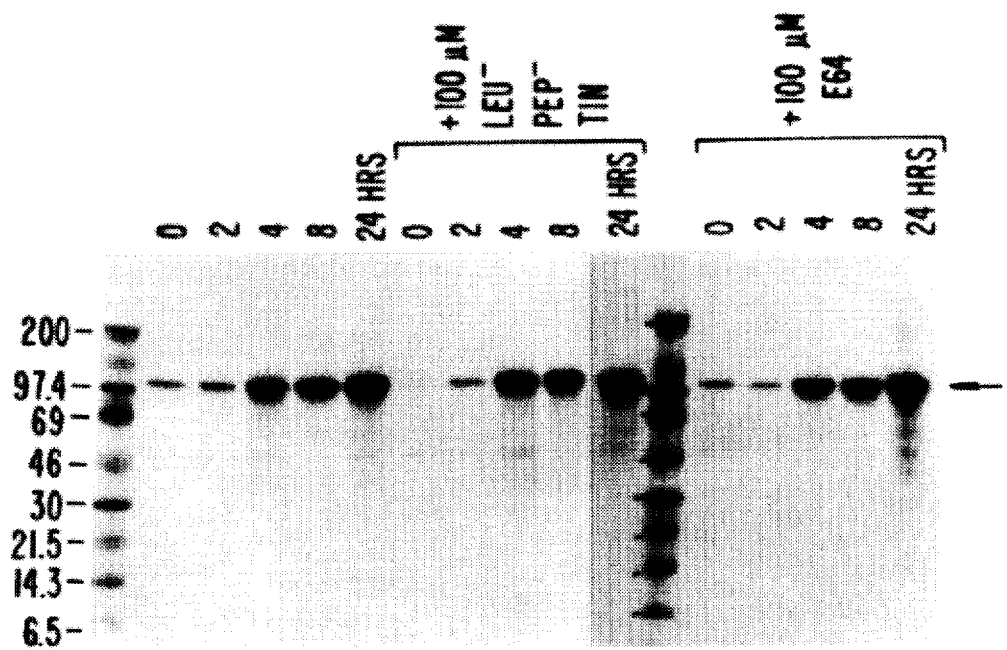

The results are shown in FIGS. 2A and 2B. In the leupeptin- or E-64-treated cells, a new, diffuse protein band, electrophoretically migrating slightly slower than the 21.5 kD standard marker, is evident at 2 hours (lanes 9 and 15). At the same level of exposure, no evidence of the band was seen in the control cell immunoprecipitates (lanes 3 and 4). In addition, the approximately 9 kD cCTF produced in the cell as a result of maturation of amyloid precursor peptide through the secretory pathway appears to accumulate, along with a number of slightly slower migrating bands (estimated molecular weights 10–14 kD), in the cells treated with either of the protease inhibitors, but not in the control cells. We conclude from this experiment that both of the protease inhibitors inhibit the degradation (but not the formation) of an approximately 22 kD fragment which is being generated from full-length amyloid precursor protein from a non-secretory metabolic pathway. As evident in FIGS. 2A and 2B, neither leupeptin nor E-64 interfere with secretion. The inability to visualize the 22 kD fragment in the absence of protease inhibitor treatment may result from very rapid degradation.

Example 2

Lysosomotropic agents block the formation of the 22 kD fragment.

Figure 3:
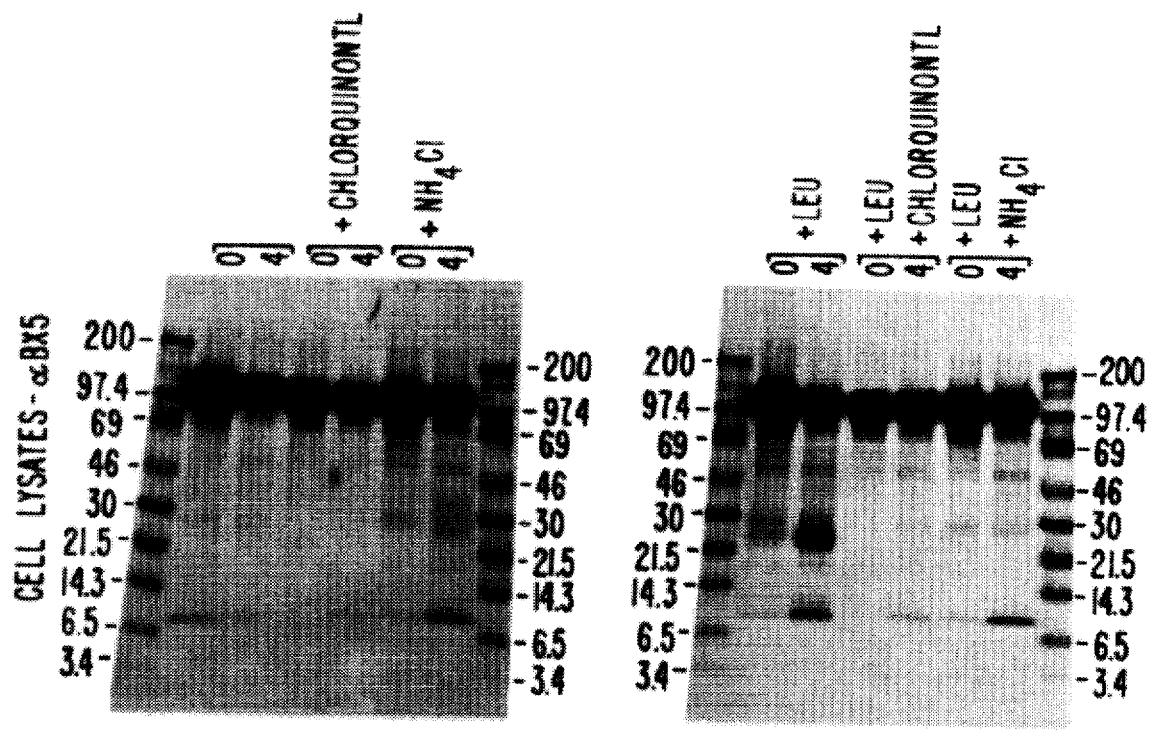
FIG. 3 is an electrophoretic gel autoradiograph which illustrates the loss of the approximately 22 kD band when the tested cells are exposed to ammonium chloride or chloroquine.

As in Example 1, 293 cells expressing the 751 isoform of amyloid precursor protein were plated, then treated for 16 hours with leupeptin. The cells were labelled for 1 hour as described, but during the chase, the medium was supplemented with 10 mM ammonium chloride or 0.1 mM chloroquine to raise the intralysosomal pH and render the lysosomal proteases dysfunctional. Samples were immunoprecipitated and electrophoresed as described before, the gels fixed, and then exposed to autoradiography film. In some experiments, these cells were not treated with leupeptin, but were exposed to the above concentrations of ammonium chloride or chloroquine during the chase. FIG. 3 shows that the 22 kD polypeptide was not detected when the ammonium chloride was added to the leupeptin-containing medium, although stabilization of the cCTF did occur. Treatment with ammonium chloride only (during the chase) did not lead to any detectable generation of the 22 kD fragment, but was found to stabilize the cCTF arising out of the secretory pathway. Similar results were obtained with chloroquine. Thus, co-treatment of cells with leupeptin and either of the two agents which raise intralysosomal pH will inhibit the formation of the 22 kD peptide with little effect on secretion. It appears that generation of the 22 kD peptide is dependent on maintenance of acidic pH and likely occurs in an acidic intracellular compartment, probably the endosome-lysosome.

Example 3

Immunoprecipitation of the approximately 22 kD fragment with anti-APP antibodies.

In order to verify that the approximately 22 kD fragment is a degradation of amyloid precursor protein, various antibodies raised to different portions of the precursor protein were used to define epitopes present on the fragment. The antibodies used were as follows.

| Antibody | Epitope |
| --- | --- |
| C7 and C8 | Polyclonal rabbit antisera raised to a synthetic peptide corresponding to the last twenty amino-acids of the amyloid precursor protein sequence; |
| 13G8 | A monoclonal antibody raised to the fusion protein BX6 (comprising residues 595–695 of amyloid precursor protein); |
| R1280 | Polyclonal rabbit antisera raised to residues 1–28 of the β-peptide; |
| 10D5 | A monoclonal antibody raised to residues 1–28 of the β-peptide; |
| 1G5 | A monoclonal antibody raised to the fusion protein BX5 (comprising residues 444–592 of amyloid precursor protein); |
| α-BX3 | Polyclonal rabbit purified antibody raised in rabbits to a fusion protein containing residues 20–304 of amyloid precursor protein; |
| α-BX5 | Polyclonal rabbit purified antibody raised to a fusion protein containing residues 444–592 of amyloid precursor protein; and |
| α-BX6 | Polyclonal rabbit purified antibody raised to a fusion protein containing residues 592–695 of amyloid precursor protein. |

Figure 4:
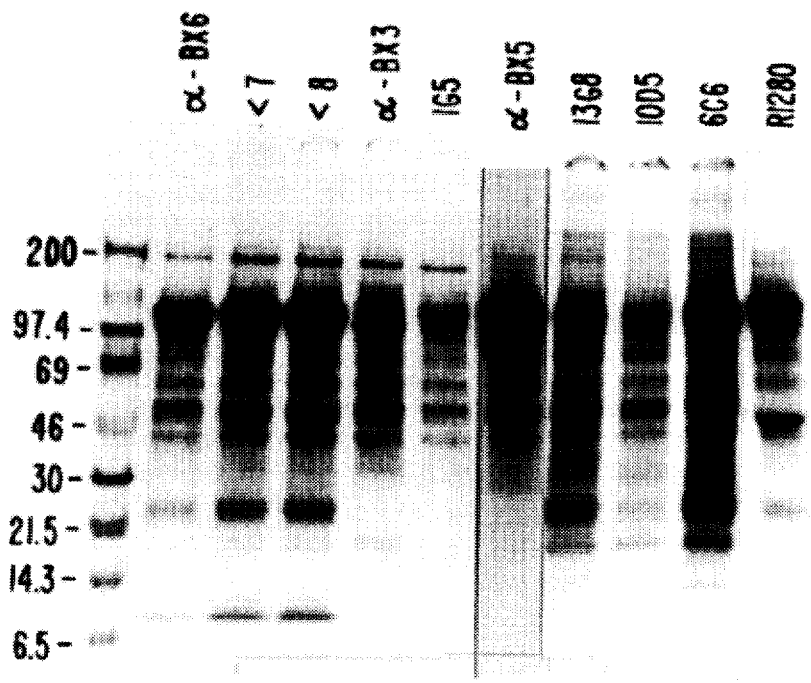
FIG. 4 is an electrophoretic gel autoradiograph which illustrates immunoprecipitation of the approximately 22 kD preamyloid intermediate polypeptide by antibodies which bind to the carboxy terminal end (but not the amino terminal side) of the amyloid precursor protein.

As described in Example 1, 293 cells were plated and treated with leupeptin for 16 hours, metabolically labelled for 1 hour, and then chased for 4 hours. Individual aliquots (approximately 40 µg) of total protein obtained at 4 hours were separately immunoprecipitated with each of the described antibodies and, then analyzed by electrophoresis on 10–20% Tris-Tricine gels and autoradiography. FIG. 4 shows that the approximately 22 kD fragment was immunoprecipitated with each of the carboxy-terminal antibodies (α-BX6; C7; C8; and 13G8), and both of the β-peptide antibodies (R1280; and 10D5), but not with the more amino-terminal antibodies (1G5; and α-BX3). Polyclonal antibody α-BX5 did not immunoprecipitate the 22 kD preamyloid intermediate peptide. Thus, the 22 kD preamyloid intermediate peptide appears to be different than the 22 kD peptide fragment described in Tamaoka et al. (1991) supra. Thus, it appears that the approximately 22 kD peptide extends to the carboxy terminal of amyloid precursor protein and contains the entire β-amyloid peptide sequence (since it is recognized by both of the β-peptide antibodies). It is not known how far it extends beyond the amino-terminal region of the β-peptide, since none of the more amino-terminal antibodies recognize this fragment. It is clearly larger than fragments which begin at the amino-terminal residue of the β-peptide (in this electrophoretic separation system, such fragments have an apparent mobility slightly faster than that of the 14 kD marker). Therefore, the 22 kD polypeptide is a processing intermediate of amyloid precursor protein which contains the full β-peptide sequence and an unknown number of amino acids amino-terminal to this sequence.

In order to substantiate identification of the 22 kD polypeptide as a preamyloid intermediate in a non-secretory pathway of amyloid precursor protein degradation in transfected human 293 cells, other cell lines were tested for the accumulation of the 22 kD preamyloid intermediate, in the presence or absence of protease inhibitors. These cell lines were: non-transfected 293 cells; PC-12 (rat adrenal pheochromocytoma); CHO-K1 (Chinese hamster ovary); B-103-API 5 (rat neuronal cell line, obtained from David Schubert, Salk Institute, and stably transfected with APP751, Nature (1974) 249:224–227); H4 (human neuroglioma).

In each case, cells were incubated with either leupeptin (0.1 mM), E-64 (0.1 mM), or the aspartic protease inhibitor pepstatin (0.1 mM). Leupeptin or E-64 were also combined with pepstatin at the above concentrations in a co-treatment paradigm. Cells were exposed to inhibitor for 24 hours, then lysed, and extracts prepared as described earlier. These extracts were not metabolically labelled or immunoprecipitated, but approximately 100 μg protein from each extract was treated with an aliquot of an immuno-affinity matrix (prepared by cross-linking monoclonal antibody 13G8 to Protein-A-agarose). Extracts were discarded, the matrix aliquot washed, and bound proteins then released by boiling in Laemmli sample buffer. Each sample was then electrophoresed on 10–20% Tris-Tricine gels, transferred by standard protocols onto Immobilon-P transfer membrane (Millipore Corp., Bedford, Mass.), and then Western probed with α-BX6 antibody. The blots were subsequently developed with alkaline phosphatase-conjugated goat anti-rabbit IgG, and BCIP+NBT chomogenic substrate (both from Bio-Rad Laboratories, Hercules, Calif.). Results obtained from these experiments are summarized below:

| Cell Line | Peptide | Protease Inhibitor(s)[3] | | | | |
| --- | --- | --- | --- | --- | --- | --- |
| | | Leu | E-64 | Pep | Leu + Pep | E-64 + Pep |
| PC12 | 22-CTF[1] | + | + | – | +++ | +++ |
| | cCTF[2] | + | + | –/+ | +++ | +++ |
| CHO-K1 | 22-CTF | – | – | – | +/– | +/– |
| | cCTF | + | + | – | ++ | ++ |
| 293 | 22-CTF | + | + | – | ++ | ++ |
| | cCTF | + | + | – | ++ | ++ |
| B-103 | 22-CTF | + | + | – | ++ | ++ |
| | cCTF | + | + | – | ++ | ++ |
| H4 | 22-CTF | – | – | – | – | – |
| | cCTF | + | + | – | ++ | ++ |

[1] 22 kD preamyloid intermediate polypeptide.
[2] 9 kD cCTF.
[3] "+" indicates a detectable enhancement of signal over untreated cells;
"++" indicates a moderate enhancement of signal over untreated cells;
"+++" indicates a strong enhancement of signal over untreated cells; and
"+/–" indicates an equivocal enhancement of signal over untreated cells.

From these results, it is apparent that multiple cell types show evidence of accumulation of the 22 kD preamyloid intermediate, and stabilization of the cCTF and intermediate MW CTF's, when treated with the cysteine protease inhibitors leupeptin or E-64. Co-treatment of all the cells with the cysteine protease inhibitors, along with the aspartic protease inhibitor pepstatin (but not with pepstatin alone) leads to a marked enhancement of all CTFs, especially the 22 kD preamyloid intermediate polypeptide and the cCTF, indicating that lysosomal proteases from different classes act synergistically in the normal turnover of such fragments.

Although the foregoing invention has been described in detail for purposes of clarity of understanding, it will be obvious that certain modifications may be practiced within the scope of the appended claims.

What is claimed is:

1. A method for identifying β-amyloid production inhibitors, said method comprising:
culturing mammalian cells which produce amyloid precursor protein in the presence of a protease inhibitor present in an amount sufficient to cause intracellular accumulation of an approximately 22 kD preamyloid intermediate which can be recognized by an antibody that recognizes a carboxy-terminal fragment of amyloid precursor protein containing the entire β-amyloid peptide sequence;
introducing to the cultured cells a plurality of test compounds, wherein each test compound is introduced to a separate population of said cultured cells; and
identifying test compounds which cause a change in the accumulation of the approximately 22 kD preamyloid intermediate,
whereby test compounds which cause a change are candidates as β-amyloid production inhibitors.

2. A method as in claim 1, wherein the cells are from a human cell line.

3. A method as in claim 2, wherein the cells have been modified to overexpress amyloid precursor protein.

4. A method as in claim 1, wherein the cells are cultured in the presence of a protease inhibitor selected from the group consisting of leupeptin, E-64, and L-transepoxysuccinyl-L-leucylamido-3-methyl-butaine present in an amount sufficient to cause the intracellular accumulation of the approximately 22 kD preamyloid intermediate.

5. A method as in claim 4 wherein the protease inhibitor comprises both a cysteine protease inhibitor and an aspartic protease inhibitor.

6. A method as in claim 4, wherein the protease inhibitor is present at a concentration in the range from 0.1 μM to 1 mM.

7. A method as in claim 1, wherein the cells are exposed to the test compounds at concentrations from 1 μM to 1 mM.

8. A method as in claim 4, wherein the cells are exposed concurrently to the protease inhibitor and each test compound.

9. A method as in claim 1 wherein the test compounds comprise biological polymers selected from the group consisting of polypeptides, polysaccharides, and polynucleotides.

10. A method as in claim 1, wherein the test compounds which cause a change in the accumulation of the approximately 22 kD preamyloid intermediate are identified by comparing the accumulation of the approximately 22 kD preamyloid intermediate in a population of the cells exposed to a test compound to the accumulation in a population of the cells free from the test compound.

11. A method as in claim 10, wherein the change is increased accumulation in cells exposed to the test compound compared to accumulation in the absence of the test compound.

12. A method as in claim 10, wherein the change is decreased accumulation in cells exposed to the test compound compared to accumulation in the absence of the test compound.

13. A method for identifying β-amyloid production inhibitors, said method comprising:
culturing mammalian cells which produce amyloid precursor protein in a growth medium;

introducing a protease inhibitor to the growth medium which enhances intracellular accumulation of an approximately 22 kD preamyloid intermediate which can be recognized by an antibody that recognizes a carboxy-terminal fragment of amyloid precursor protein containing the entire β-amyloid peptide sequence;

introducing a test compound to the growth medium; and detecting changes in the intracellular accumulation of the approximately 22 kD preamyloid intermediate which result from the exposure of the cells to the test compound in the medium, whereby test compounds which cause a change are candidates as β-amyloid production inhibitors.

14. A method as in claim 13, wherein the cells are from a human cell line.

15. A method as in claim 14, wherein the cells have been modified to overexpress amyloid precursor protein.

16. A method as in claim 13, wherein the substance comprises a protease inhibitor selected from the group consisting of leupeptin, E-64, and L-trans epoxysuccinyl-L-leucylamido- 3-methyl-butiane present in an amount sufficient to cause the intracellular accumulation of the approximately 22 kD preamyloid intermediate.

17. A method as in claim 16, wherein the protease inhibitor comprises both a cysteine protease inhibitor and an aspartic protease inhibitor.

18. A method as in claim 16, wherein the protease inhibitor is present at a concentration in the range from 0.1 µM to 1 mM.

19. A method as in claim 13, wherein the cells are exposed to the test compound at a concentration from 1 µM to 1 mM.

20. A method as in claim 13, wherein the cells are exposed concurrently to the substance and the test compound.

21. A method as in claim 13, wherein the test compound comprises a biological polymer, selected from the group consisting of polypeptides, polynucleotides, and polysaccharides.

22. A method as in claim 13, wherein changes in the intracellular accumulation are detected by measuring the accumulation of the approximately 22 kD preamyloid intermediate in cultured cells exposed to the test compound, measuring the accumulation in genetically identical cells cultured under the same conditions but not exposed to the test compound, and comparing the two measured values.

23. A method as in claim 22, wherein exposure to the test compound results in an increase in the measured value of accumulation in the cells exposed to the test compound compared to the cells not exposed to the test compound.

24. A method as in claim 22, wherein exposure to the test compound results in a decrease in the measured value of accumulation in the cells exposed to the test compound compared to the cells not exposed to the test compound.

25. A method for assaying a test compound for the ability to inhibit β-amyloid production in cells, said method comprising:

exposing the test compound to mammalian cells cultured in the presence of a protease inhibitor under conditions which cause the intracellular accumulation of an approximately 22 kD preamyloid intermediate which can be recognized by an antibody that recognizes a carboxy-terminal fragment of amyloid precursor protein containing the entire β-amyloid peptide sequence; and detecting a change in the accumulation of the approximately 22 kD preamyloid intermediate relative to the accumulation in control cells which are cultured under the same condition but not exposed to the test compound, whereby test compounds which cause a change are candidates as β-amyloid production inhibitors.

26. A method as in claim 25, wherein the cells are from a human cell line.

27. A method as in claim 26, wherein the cells have been modified to overexpress amyloid precursor protein.

28. A method as in claim 25, wherein the cells are cultured in the presence of a protease inhibitor selected from the group consisting of leupeptin, E-64, and L-transepoxysuccinyl-L-leucylamido- 3-methyl-butaine present in an amount to cause the intracellular accumulation of the approximately 22 kD preamyloid intermediate.

29. A method as in claim 28, wherein the protease inhibitor comprises both a cysteine protease inhibitor and an aspartic protease inhibitor.

30. A method as in claim 28, wherein the protease inhibitor is present at a concentration in the range from 0.1 µM to 1 mM.

31. A method as in claim 25, wherein the cells are exposed to the test compound at a concentration from 1 µM to 1 mM.

32. A method as in claim 28, wherein the cells are exposed concurrently to the protease inhibitor and the test compound.

33. A method as in claim 25, wherein the test compound comprises a biological polymer, selected from the group consisting of polypeptides, polynucleotides, and polysaccharides.

34. A method as in claim 25, wherein detecting the change in accumulation comprises:

measuring the accumulation of the approximately 22 kD preamyloid intermediate in the cells over a preselected time interval;

measuring the accumulation of the approximately 22 kD preamyloid intermediate in the control cells over the preselected time interval; and comparing the two measured values.

35. A method as in claim 34, wherein the accumulation of the approximately 22 kD preamyloid intermediate is measured by immunoprecipitation followed by gel electrophoresis.

36. A method as in claim 34, where the preselected time interval is from 0.5 to 24 hours.

37. A method as in claim 34, wherein the exposure to the test compound results in an increase in the measured value of accumulation in the cells exposed to the test compound compared to the cells not exposed to the test compound.

38. A method as in claim 34, wherein exposure to the test compound results in a decrease in the measured value of accumulation in the cells exposed to the test compound compared to the cells not exposed to the test compound.

* * * * *